(12) United States Patent
Parrow et al.

(10) Patent No.: US 7,285,392 B2
(45) Date of Patent: Oct. 23, 2007

(54) METHODS FOR IDENTIFYING ACTIVE COMPOUNDS

(75) Inventors: Vendela Parrow, Uppsala (SE); Lotta Moréus, Stockholm (SE)

(73) Assignee: Biovitrum AB, Stockholm (SE)

( * ) Notice: Subject to any disclaimer, the term of this patent is extended or adjusted under 35 U.S.C. 154(b) by 25 days.

(21) Appl. No.: 10/878,773

(22) Filed: Jun. 28, 2004

(65) Prior Publication Data

US 2005/0042691 A1  Feb. 24, 2005

Related U.S. Application Data

(60) Provisional application No. 60/497,003, filed on Aug. 20, 2003.

(30) Foreign Application Priority Data

Jun. 30, 2003  (SE) .................................... 0301917

(51) Int. Cl.
*G01N 33/53* (2006.01)
(52) U.S. Cl. ..................... 435/7.2; 435/7.1; 435/7.21; 435/7.8; 436/501; 436/503
(58) Field of Classification Search ..................... None
See application file for complete search history.

(56) References Cited

FOREIGN PATENT DOCUMENTS

| WO | WO 98/41872 | 9/1998 |
|---|---|---|
| WO | WO 00/52153 | 9/2000 |
| WO | WO 00/66632 | 11/2000 |
| WO | WO 03/031651 | 4/2003 |

OTHER PUBLICATIONS

Phosphorylation. Wikipedia website. wikipedia.org/wiki/Phosphorylation; accessed Jun. 2, 2006; pp. 1-2.*
Ozaki et al., JBC. 2002; 277: 29355-29358.*
sigma-aldrich.com/ehandbook, Cytokine Receptors (Hematopoeitin Receptor Family, pp. 174-179.*
Denson et al., J Clin Invest. 107:1451-1458, Jul. 27, 2007.*
Ram et al., J Biol Chem. 1996; 271: 5929-5940.*
Adams, Biochem J. 1999; 344: 867-872.*
Bichell, D.P., Kikuchi, K., Rotwein, P. (1992). Growth Hormone Rapidly Activates Insulin-Like Growth Factor I Gene Transcription in vivo. *Mol. Endocrin.* 6:1899-1908.
Bromberg (2000). Signal transducers and activators of transcription as regulators of growth, apoptosis and breast development. *Breast Cancer* 2:86-90.
Catlett-Falcone et al., (1999). STAT proteins as novel targets for cancer therapy. *Current Opinion in Oncology* 11:490-496.
Clevenger, C.V., Furth, P., Hankinson, S.E., Shuler, L. (2003). The role of prolactin in mammary carcinoma. *Endocrine Rev.* 24:1-27.
Dignam, J.D., Lebowitz, R. M., Roeder, R. (1983). Accurate transcription initiation by RNA polymerase II in a soluble extract from isolated mammalian nuclei. *Nucl. Acids Res.* 11:1475-1489.
Graichen, R., Sandstedt, J., Goh, E. L. K., Isaksson, O. G. P., Törnell, J., Lobie, P. E. (2003). the Growth Hormone-binding Protein Is a Location-dependent Cytokine Receptor Transcriptional Enhancer. *J. Biol. Chem.* 278:6346-6354.
Helander, H., Gustafsson, J-Å., Mode, A. (2002). Possible involvement of truncated signal transducer and activator of transcription-5 in the GH pattern-dependent regulation of CYP2C12 gene expression in rat liver. *Mol. Endocrinology* 16:1598-1611.
Horvath (2000). STAT proteins and transcriptional responses to extracellular signals. *TIBS* 25:496-501.
Jiang, L.-W., Schindler, M. (1990). Nucleocytoplasmic transport is enhanced concomitant with nuclear accumulation of epidermal growth factor (EGF) binding activity in both 3T3-1 and EGF receptor reconstituted NR-6 fibroblasts. *J. Cell Biol.* 110:559-568.
Johnson et al., (2001). Differential expression of suppressors of cytokine signaling genes in response to nutrition and growth hormone in the septic rat. *Journal of Endocrinology* 169:409-415.
Le Stunff, C., Thomas, M. J., Rotwein, P. (1995). Rapid Activation of Rat Insulin-Like Growth Factor-I Gene Transcription by Growth Hormone Reveals No Changes in Deoxyribonucleic Acid-Protein Interactions within the Second Promoter. *Endocrinology* 136:2230-2237.
Lobie, P. E., Wood, T. J. J., Chen, C. M., Waters, M. J., Norstedt, G. (1994). Nuclear Translocation and Anchorage of the Growth Hormone Receptor. *J. Biol. Chem.* 269:31735-31746.
Nolten, L.A., Steenbergh, P.H., Sussenbach, J.S. (1995). Hepatocyte nuclear factor 1α activates promoter 1 of the human insulin-like growth factor 1 gene via two distinct binding sites. *Mol. Endocrinology* 9: 1488-1499.
Pfisterer, P., Ehlermann, J., Hegen, M., Schorle, H. (2002). A Subtractive Gene Expression Screen Suggests a Role of Transcription Factor AP-2α in Control of Proliferation and Differentiation. *J. Biol. Chem.* 277:6637-6644.
Podlecki, D.A, Smith, R.M., Kao, M., Tsa, M., Huecksteadt, T., Brandenburg, D., Lasher, R.S., Jarret, L., Olefsky, J.M. (1987). Nuclear translocation of the insulin receptor. *J. Biol. Chem.* 262:3362-3368.
Thomas, et al., (1994) Rapid activation of rat insulin-like growth factor-1 gene transcription by growth hormone reveals no alterations in deoxyribonucleic acid-protein interactions within the major promoter. *Endocrinology* 135:1584-1592.
Wang et al., (1997). Characterization of the rat insulin-like growth factor I gene promoters and identification of a minimal exon 2 promoter 1. *Endocrinology* 138(4):1528-1536.
Werling, U., Schorle, H. (2002). Transcription Factor gene *AP-2γ* Essential for Early Murine Development. *Mol. Cell. Biol.* 22:3149-3156.
Zhang, Y., Guan, R., Jiang, J., Kopchick, J.J., Black, R.A., Baumann, G., Frank, S. (2001). Growth hormone (GH)-induced dimerization inhibits phorbol ester-stimulated GH receptor proteolysis. *J. Biol. Chem.* 276: 24565-24573.

* cited by examiner

*Primary Examiner*—Elizabeth C. Kemmerer
*Assistant Examiner*—Christina Borgeest
(74) *Attorney, Agent, or Firm*—Fish & Richardson P.C.

(57) ABSTRACT

The present invention relates to methods for identifying agents that modulate the effect of cytokine class I receptor binding compounds, by inhibiting the interaction between the cytokine class I receptor and nuclear factors. The agents are useful for decreasing IGF-1 levels in a cell, and for the treatment of medical disorders caused by hormone dysregulation, such as growth hormone or prolactin dysregulation.

7 Claims, 5 Drawing Sheets

GHR - transfected WRL - 68
Pr2F DNA - probe

PRLR - transfected WRL - 68
Pr2F DNA - probe

SEQUENCE LISTING

```
<160> NUMBER OF SEQ ID NOS: 14

<210> SEQ ID NO 1
<211> LENGTH: 34
<212> TYPE: DNA
<213> ORGANISM: Artificial Sequence
<220> FEATURE:
<223> OTHER INFORMATION: PCR oligonucleotide

<400> SEQUENCE: 1
tacgcttcta ctaatccatg ttctgagaaa tcat                                34

<210> SEQ ID NO 2
<211> LENGTH: 34
<212> TYPE: DNA
<213> ORGANISM: Artificial Sequence
<220> FEATURE:
<223> OTHER INFORMATION: PCR oligonucleotide

<400> SEQUENCE: 2
atgatttctc agaacatgga ttagtagaag cgta                                34

<210> SEQ ID NO 3
<211> LENGTH: 22
<212> TYPE: DNA
<213> ORGANISM: Artificial Sequence
<220> FEATURE:
<223> OTHER INFORMATION: PCR oligonucleotide

<400> SEQUENCE: 3
tgtcgaatgc aaatcactag aa                                             22

<210> SEQ ID NO 4
<211> LENGTH: 22
<212> TYPE: DNA
<213> ORGANISM: Artificial Sequence
<220> FEATURE:
<223> OTHER INFORMATION: PCR oligonucleotide

<400> SEQUENCE: 4
ttctagtgat ttgcattcga ca                                             22

<210> SEQ ID NO 5
<211> LENGTH: 26
<212> TYPE: DNA
<213> ORGANISM: Artificial Sequence
<220> FEATURE:
<223> OTHER INFORMATION: PCR oligonucleotide

<400> SEQUENCE: 5
```
gatcgaactg accgcccgcg gcccgt 26

<210> SEQ ID NO 6
<211> LENGTH: 26
<212> TYPE: DNA
<213> ORGANISM: Artificial Sequence
<220> FEATURE:
<223> OTHER INFORMATION: PCR oligonucleotide

<400> SEQUENCE: 6
acgggccgcg ggcggtcagt tcgatc 26

<210> SEQ ID NO 7
<211> LENGTH: 21
<212> TYPE: DNA
<213> ORGANISM: Artificial Sequence
<220> FEATURE:
<223> OTHER INFORMATION: PCR oligonucleotide

<400> SEQUENCE: 7
cgcttgatga gtcagccgga a 21

<210> SEQ ID NO 8
<211> LENGTH: 21
<212> TYPE: DNA
<213> ORGANISM: Artificial Sequence
<220> FEATURE:
<223> OTHER INFORMATION: PCR oligonucleotide

<400> SEQUENCE: 8
ttccggctga ctcatcaagc g 21

<210> SEQ ID NO 9
<211> LENGTH: 33
<212> TYPE: DNA
<213> ORGANISM: Artificial Sequence
<220> FEATURE:
<223> OTHER INFORMATION: PCR oligonucleotide

<400> SEQUENCE: 9
gatctagatg ctttcacaaa ccccacccac aaa 33

<210> SEQ ID NO 10
<211> LENGTH: 33
<212> TYPE: DNA
<213> ORGANISM: Artificial Sequence
<220> FEATURE:
<223> OTHER INFORMATION: PCR oligonucleotide

<400> SEQUENCE: 10
agcttttgtg ggtgggttt gtgaaagcat cta 33

<210> SEQ ID NO 11
<211> LENGTH: 62
<212> TYPE: DNA
<213> ORGANISM: Artificial Sequence
<220> FEATURE:
<223> OTHER INFORMATION: PCR oligonucleotide

<400> SEQUENCE: 11
ctagatgctt tcacaaaccc cacccacaaa atagatgctt tcacaaaccc cacccacaaa 60
ac 62

<210> SEQ ID NO 12
<211> LENGTH: 70

-continued

```
<212> TYPE: DNA
<213> ORGANISM: Artificial Sequence
<220> FEATURE:
<223> OTHER INFORMATION: PCR oligonucleotide

<400> SEQUENCE: 12
tcgagttttg tgggtggggt ttgtgaaagc atctattttg tgggtggggt ttgtgaaagc    60
atctaggtac                                                          70

<210> SEQ ID NO 13
<211> LENGTH: 54
<212> TYPE: DNA
<213> ORGANISM: Artificial Sequence
<220> FEATURE:
<223> OTHER INFORMATION: PCR oligonucleotide

<400> SEQUENCE: 13
cgatcgaact gaccgcccgc ggcccgtgat cgaactgacc gcccgcggcc cgtc          54

<210> SEQ ID NO 14
<211> LENGTH: 62
<212> TYPE: DNA
<213> ORGANISM: Artificial Sequence
<220> FEATURE:
<223> OTHER INFORMATION: PCR oligonucleotide

<400> SEQUENCE: 14
tcgagacggg ccgcgggcgg tcagttcgat cacgggccgc gggcggtcag ttcgatcggt    60
ac                                                                  62
```

METHODS FOR IDENTIFYING ACTIVE COMPOUNDS

CROSS REFERENCE TO RELATED APPLICATIONS

This application claims priority from Swedish Patent Application No. 0301917-1, filed Jun. 30, 2003, and U.S. Provisional Patent Application No. 60/497,003, filed Aug. 20, 2003. The prior applications are incorporated herein by reference in their entirety.

TECHNICAL FIELD

The present invention relates to methods for identifying agents that modulate the effect of cytokine class I receptor binding compounds, said agents being useful for decreasing IGF-1 levels in a cell, and for the treatment of medical disorders caused by hormone dysregulation, such as growth hormone or prolactin dysregulation.

BACKGROUND

Growth hormone (GH) is secreted from the adenohypophysis (anterior pituitary gland) and has a variety of target tissues. GH has a common range of actions including somatic growth, differentiation and intermediary metabolism, effects that are mediated by GH-induced insulin-like growth factor-1 (IGF-1) (Bichell et al., 1992). IGF-1 is the major regulator of post-natal growth, and has both endocrine and paracrine action on different tissues.

GH induces transcription of different genes by binding to a membrane-associated receptor, the growth hormone receptor (GHR), which belongs to the superfamily of cytokine receptors (Graichen et al., 2003). These receptors lack intrinsic catalytic activity but are associated to cytosolic proteins with tyrosine-kinase activity. The receptors possess a single membrane-spanning domain and they exist as monomers that dimerize and become activated upon ligand binding. Several intracellular second messengers have been implicated in the signal transduction of GH, including calcium ions, phospholipase C, phospholipase A2, G-proteins, protein kinase C (PKC), Janus kinase 2 (JAK2) and signal transducer and activator of transcription (STAT) 1, 3 and 5 (Wood, 1996).

The signal transduction of GH has been investigated in the serine protease inhibitor (SPI) 2.1 gene, where activation is mediated through phosphorylation of JAK2 and STAT5 (Wood, 1996). When GHR becomes activated upon ligand binding the tyrosine kinase JAK2, which is associated to the GHR intracellular part, becomes phosphorylated and then phosphorylates the GHR itself. This leads to phosphorylation of STAT5, which homodimerizes, translocates to the nucleus and binds a specific sequence in the SPI 2.1 promoter called the GH-response element (GHRE), thereby activating gene transcription.

To regulate the numbers of GHR on the cell surface, the GHR is internalized in the cell by endocytosis and transported to lysosomal vesicles for destruction. However, the GHR has also been reported to get internalized and translocate to the nucleus upon GH-stimulation (Lobie, Wood 1994). It has been suggested that GHR itself might be involved in gene regulation. Interestingly, the nuclear translocation of both GH and the GHR is independent of JAK2 (Graichen et al., 2003), which suggests that this nuclear translocation might be an alternative signal transduction pathway independent of the JAK-STAT pathway.

Investigation of the two IGF-1 promoters reveals that no changes can be seen in DNA-protein interactions when rat hepatic IGF-1 is activated by GH (LeStunff et al., 1995, Thomas et al., 1994), and this together with the fact that GH induce a rapid activation of IGF-1 transcription (Bichell et al., 1992) suggests a GH-induced modification of pre-existing transcription factors bound to the DNA. One of the protein-bound DNA-sites in promoter 2 has been found to be a possible binding site for the transcription factor AP2, and the transcription factor OCT1 has also been suggested to bind to this promoter region (LeStunff et al., 1995). The transcription factor AP2 belongs to a family with four members, which all have been implicated as tissue-specific effectors of proliferation and differentiation during embryogenesis (Pfisterer et al., 2002; Werling and Schorle 2002). OCT1 is a ubiquitous transcription factor found in most mammalian cell types, where it activates transcription of a variety of genes.

DISCLOSURE OF THE INVENTION

Figure 1A:
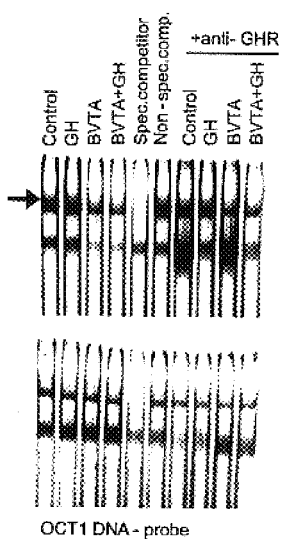
FIG. 1A depicts the results of electrophoresis mobility shift assays (EMSA) in nuclear extracts from growth hormone receptor (GHR) transfected and non-transfected WRL-98 cells incubated with an anti-GHR antibody and OCT1 DNA probes (SEQ ID NOS:3 and 4).

It has been found that the full-length growth hormone (GH) receptor is present in isolated nuclei from rat hepatocytes and a cultured human liver cell-line by immunocytochemistry and Western blotting. Electrophoretic mobility shift assays indicate that the receptor interacts with other transcription factors, as shown by an increased amount of super shift observed in the presence of GH-receptor transfected cells. This interaction is down regulated by treatment with BVTA (N-[5-(aminosulfonyl)-2-methylphenyl]-5-bromo-2-furamide), a GH-receptor binding compound, which causes a decrease of GH-inducible mRNA. Thus, it is proposed that the nuclear GH-receptor is functional and a part of the protein complexes regulating the level of transcription.

In a first aspect, this invention provides a method for identifying an agent that modulates an interaction between a cytokine class I receptor and a nuclear factor, the method comprising: (i) contacting a cell with a candidate agent; and (ii) determining whether the candidate agent modulates an interaction between a cytokine class I receptor and a nuclear factor that interacts with the receptor; with the proviso that the nuclear factor is other than STAT5. An agent identified by such a method can be used, for example, for the treatment or prevention of a medical disorder caused by dysregulation of a cytokine class I receptor binding compound.

The method can optionally include the following steps: (i) contacting the cell with the candidate agent, wherein the candidate agent modulates the interaction between the cytokine class I receptor and the nuclear factor; (ii) measuring, in the presence of the candidate agent, a biological effect of a cytokine class I receptor binding compound in the cell; and (iii) determining whether the candidate agent modulates the biological effect of the cytokine class I receptor binding compound in the cell. In some embodiments, the candidate agent inhibits the interaction between growth hormone receptor and the nuclear factor. In other embodiments, the candidate agent stimulates the interaction between growth hormone receptor and the nuclear factor.

The method can optionally include a step of determining the expression of a reporter gene coupled to a promoter comprising a response element for a nuclear factor selected from the group consisting of AP2, OCT1, and Pr2F.

Candidate agents that can be used in the methods described herein include, for example, polypeptides, peptides, antibodies or antibody fragments, non-peptide compounds, carbohydrates, small molecules, lipids, single or double stranded DNA, single or double stranded RNA, antisense nucleic acid molecules, and ribozymes.

The identification methods described herein can be carried out in vitro or in vivo. For in vitro methods, the identification can be made using a cell based system or a cell free system.

In another aspect, the invention features a method for identifying a nuclear factor that interacts with a cytokine class I receptor, the method comprising: (i) transfecting a cell with a nucleic acid encoding a cytokine class I receptor; (ii) preparing a nuclear extract from the cell; (iii) incubating the nuclear extract with a labeled oligonucleotide probe that binds to a candidate nuclear factor; (iv) separating the reaction mixture in a polyacrylamide gel; and (v) detecting bands corresponding to protein-DNA complexes. The method can optionally include a step of, prior to preparing the nuclear extract, stimulating the cell with a cytokine class I receptor binding compound.

Other methods for identifying nuclear factors include transfecting cells with a reporter construct wherein the nuclear factor oligonucleotide is part of the promoter regulating transcription of the reporter gene. The cells are stimulated with a cytokine class I receptor binding compound and the reporter gene activity is measured.

The nuclear factor is optionally a DNA binding protein, such as AP2, OCT1, or Pr2F.

A method according to the invention can comprise the determination whether the candidate agent modulates the effect of growth hormone in the cell. In one embodiment of the invention, such determination comprises determining the expression of a reporter gene coupled to a promoter, e.g., the SPI 2.1, AP2, OCT-1 or Pr2F promoter.

Reporter genes such as, for example, luciferase, β-galactosidase, alkaline phosphatase, chloramphenicol acetyl transferase (CAT), Green Fluorescent Protein and other members of the Reef Coral Fluorescent Protein (RCFP) family, can be used to determine transcriptional activity in screening assays according to the invention (see, for example, Goeddel (ed.), Methods Enzymol., Vol. 185, San Diego: Academic Press, Inc. (1990)).

Those agents identified according to the methods described herein that modulate the effect of growth hormone in a cell can be used, for example, for the treatment or prevention of a medical disorder caused by growth hormone dysregulation. Such disorders include, e.g., acromegaly, growth hormone deficiency, growth retardation associated with the Prader-Willi syndrome and Turner's syndrome, growth hormone insensitivity, wasting disorders associated with Acquired Immunodeficiency Syndrome (AIDS), and osteoporosis. Further, the agents can be used for decreasing or inhibiting the IGF-1 levels or IGF-1 production in a cell.

For the treatment of acromegaly, it is expected that the identified agent will inhibit or decrease the interaction between GHR and the nuclear factor. For the treatment of disorders related to growth hormone deficiency, such as Prader-Willi syndrome, Turner's syndrome, growth hormone insensitivity, and osteoporosis, it is expected that the identified agent will stimulate or increase the interaction between GHR and the nuclear factor.

Those agents identified according to the methods described herein that modulate the effect of prolactin in a cell can be used, for example, for the treatment or prevention of a medical disorder caused by prolactin dysregulation. Hyperprolactinemia is a disease caused by excess production and secretion of prolactin, and results in clinical symptoms such as suppression of reproductive function and galactorrhea. As a cause of hyperprolactinemia, prolactin-secreting pituitary tumor (prolactinoma) is frequently observed. Further, it is known in the art that metabolic disorders such as obesity, hyperglycemia, hyperinsulinemia, hypercholesterolemia, hyperlipidemia and Type II diabetes are associated with aberrant patterns in the daily levels (and fluctuations) of prolactin. A subject in need of prolactin is, e.g., a person in need of stimulation of lactation, e.g., a mother; a person in need of stimulation of the immune system, e.g., a person at risk for an immune disorder, e.g., a person at risk of AIDS, or a person infected with a human immunodeficiency virus (HIV), or a person having a nutritional deficiency (see, e.g., U.S. Pat. No. 6,545,198).

For the treatment of hyperprolactinemia or prolactinoma, it is expected that the identified agent will inhibit or decrease the interaction between the prolactin receptor and the nuclear factor. For the treatment of disorders related to prolactin deficiency it is expected that the identified agent will stimulate or increase the interaction between the prolactin receptor and the nuclear factor.

In another aspect, the invention features a method for treating or preventing a medical disorder caused by dysregulation of a cytokine class I receptor binding compound, the method comprising administering to a subject in need thereof an effective amount of an agent that modulates an interaction between a cytokine class I receptor and a nuclear factor. In some embodiments, the nuclear factor is other than STAT5.

The method can optionally include a step of identifying a subject as having or being at risk of having a medical disorder described herein prior to the administration of the agent. In addition, or alternatively, the method can include a step of, following the administration of the agent, evaluating the subject for the presence of severity of one or more symptoms of the medical disorder. The amount of the agent administered to the subject can optionally be selected based upon the results of such an evaluation.

In some embodiments, the agent inhibits the interaction between the cytokine class I receptor and the nuclear factor. In other embodiments, the agent stimulates the interaction between the cytokine class I receptor and the nuclear factor.

In another aspect, the invention features a method for modulating IGF-1 transcription in a cell, the method comprising contacting a cell with an effective amount of an agent that modulates an interaction between growth hormone receptor and a nuclear factor, thereby modulating IGF-1 transcription in the cell. In some embodiments, the agent inhibits the interaction between growth hormone receptor and the nuclear factor, thereby decreasing IGF-1 transcription in the cell. In other embodiments, the agent stimulates the interaction between growth hormone receptor and the nuclear factor, thereby increasing IGF-1 transcription in the cell.

In another aspect, the invention features a method for modulating transcription in a cell, the method comprising contacting a cell with an effective amount of an agent that modulates an interaction between a cytokine class I receptor and a nuclear factor, thereby modulating transcription induced by the cytokine class I receptor in the cell, with the proviso that the nuclear factor is other than STAT5. The agent can be, for example, a compound that binds to the cytokine class I receptor and prevents or reduces the ability of the cytokine class I receptor to bind to the nuclear factor. In some embodiments, the agent inhibits the interaction between the cytokine class I receptor and the nuclear factor, thereby decreasing transcription induced by the cytokine class I receptor in the cell. In other embodiments, the agent stimulates the interaction between the cytokine class I receptor and the nuclear factor, thereby increasing transcription induced by the cytokine class I receptor in the cell.

In the methods and compositions described herein, the cytokine class I receptor can be, for example growth hormone receptor or prolactin receptor. In some embodiments, the cytokine class I receptor binding compound is growth hormone and the cytokine class I receptor is growth hormone receptor. In other embodiments, the cytokine class I receptor binding compound is prolactin and the cytokine class I receptor is prolactin receptor.

The nuclear factor used in the methods and compositions described herein can be, for example, AP2, OCT1, or Pr2F.

The agent used in the methods described herein can be, for example, a polypeptide, peptide, antibodiy or antibody fragment, non-peptide compound, carbohydrate, small molecule, lipid, single or double stranded DNA, single or double stranded RNA, antisense nucleic acid molecule, or ribozyme.

Unless otherwise defined, all technical and scientific terms used herein have the same meaning as commonly understood by one of ordinary skill in the art to which this invention belongs. Suitable methods and materials are described below, although methods and materials similar or equivalent to those described herein can also be used in the practice or testing of the present invention. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention will now be further illustrated through the description of examples of its practice. The examples are not intended as limiting in any way of the scope of the invention.

EXAMPLES

Experimental Methods

Cell culture: WRL-68 cells, a human fetal hepatic cell-line, were cultured in EMEM medium with NaHCO3 (Statens Veterinärmedicinska Anstalt), supplemented with 10% fetal bovine serum (FBS), 2% L-Glutamine, 1% Pyruvate and 1% Non essential amino acids (NEA), all from GIBCO. The cells were sub-cultivated twice weekly by trypsination to maintain a cell density of approximately 80%.

Transfection: Cells were transfected with human full-length GH-receptor (pMB1288, 2 μg/μl) by using DOTAP Liposomal Transfection Reagent (Roche), according to manufacturers manual. With this reagent a cationic liposome-mediated transfection method (lipofection) is used. T75 flasks with WRL-68 cells were transfected with 10 μg DNA for each flask. 5 μl (10 μg) DNA was diluted with 250 μl OPTIMEM1 medium (GIBCO) and mixed gently with 75 μl DOTAP reagent diluted in 175 μl OPTIMEM1 medium. The mixture was incubated for 10 minutes and then mixed gently with 10 ml OPTIMEM1 medium. Cells were washed once and then incubated for 4 hours with the DNA/DOTAP transfection mix, which was then changed to fresh culture medium. Cells were re-seeded into new culture dishes the following day.

Stimulation: Cells were stimulated two days after transfection at a confluence of approximately 80%. Starvation in serum free medium for one hour were followed by stimulation with 10 nM hGH (Genotropin, Pharmacia) for 60 minutes, 1 μM BVTA (N-[5-(aminosulfonyl)-2-methylphenyl]-5-bromo-2-furamide) for 60 minutes or with 1 μM BVTA for 60 minutes followed by 10 nM hGH for 60 minutes. Starvation in serum free medium for three hours (GHR-transfected cells) or sixteen hours (non-transfected WRL-68 cells) were followed by stimulation with 100 nM hGH for 20 minutes, 1 μM BVTA for 20 minutes or 1 μM BVTA for 20 minutes followed by 100 nM hGH for 20 minutes.

Preparation of nuclear and cytosolic fractions: Nuclear extracts were prepared according to the methods described in Dignam et al. (1983) and Ausubel et al. (1993), with the following modifications:

WRL-68 cells were scraped into ice cold PBS, pooled in 50 ml Falcon tubes and centrifuged 3000 rpm for 5 minutes. Cell pellets were re-suspended in hypotonic buffer with protease and phosphatase inhibitors (10 mM HEPES pH 7.9, 0.2 mM phenylmethylsulfonyl-fluoride (PMSF), both from Sigma, 1.5 mM $MgCl_2$, 10 mM KCl, 0.1% Nonidet P-40 (Amersham), 0.2 mM sodium orto-vanadate, 2 nM okadaic acid (Calbiochem), 1×complete protease inhibitor (Roche)), centrifuged 3000 rpm for 5 minutes and re-suspended again in hypotonic buffer. The cells were allowed to swell on ice for ten minutes and then homogenized in a Dounce homogenizer with a Teflon pestle type C. Cell lysis was confirmed in a microscope by adding trypan blue (0.4%, Sigma) to an aliquot of cells, since nuclei will stain blue in broken cells. Approximately 40 strokes were necessary to get 70-80% clean nuclear fractions. The nuclei were collected by centrifugation at 4000 rpm for 15 minutes and immediately frozen in −70° C. The supernatant was also saved in −70° C. as the cytosolic fraction.

Nuclear and cytosolic fractions were prepared from hypophysectomized Sprague Dawley rat livers (ethical license N176/02). The rats had minipumps implanted at 5 weeks of age for administration of hGH. Control animals were not stimulated and thus completely GH-deficient while GH-animals were stimulated continuously with hGH 0.12 mg/kg/day for five days. Animals were anaesthetized and livers were cut out and placed in ice-cold PBS. Livers were then cut into smaller pieces and transferred to 8 ml ice-cold hypotonic buffer with protease and phosphatase inhibitors and were allowed to swell on ice for 10 minutes. The small pieces of liver were homogenized in a Dounce homogenizer with Teflon pestle type C and the suspension was filtered through a sterile compress to get a cell-suspension. The cell-suspension was further homogenized in a Dounce homogenizer with a glass pestle. Cell lysis was confirmed in a microscope by adding trypan blue (0.4%, Sigma) to an aliquot of cells, since nuclei will stain blue in broken cells. Approximately 10-20 strokes were necessary to achieve 70-80% clean nuclear fractions. The nuclei were collected by centrifugation at 4000 rpm and 4° C. for 15 minutes. The supernatant was removed and saved as the cytosolic fraction. Pelleted nuclei and cytosol were immediately frozen in −70° C.

Extraction of nuclear proteins: To extract the proteins from the nuclei, the nuclear pellets were re-suspended in 2×lysis buffer with protease and phosphatase inhibitors (100 mM HEPES, pH 7.6, 300 mM NaCl, 10 mM EDTA (GIBCO), 2% Triton X-100 (Sigma), 0.2 mM PMSF, 0.2 mM sodium orto-vanadate, 2 nM okadaic acid, 1×complete), or EMSA buffer with inhibitors (20 mM Tris pH 8.0, 1.5 mM $MgCl_2$, 0.2 mM EDTA, 25% glycerol, 0.5 mM PMSF, 0.2 mM sodium ortho-vanadate, 2 nM okadaic acid, 1×complete protease inhibitor), depending on whether the samples should also be used in electrophoresis mobility shift assays (EMSA) or not. For an optimal protein extraction, three different methods were evaluated. Samples were left on ice for 30 minutes, treated with 1 μl DNAse at 37° C. for 15 minutes or treated with an injection needle to shear the DNA. Optimal extraction was evaluated by Western blot and protein concentration determination as described below. The samples were centrifuged at 14000 rpm and 4° C. for 10 minutes and supernatants with nuclear proteins were divided in aliquots and stored in −70° C. or used in Western Blot or EMSA assays.

Protein concentrations were determined by using a BCA Protein Assay Reagent Kit (Pierce), which uses the Biuret reaction (reduction of $Cu^{2+}$ to $Cu^{1+}$ by proteins in an alkaline medium) and a reagent containing bicinchoninic acid (BCA). Two molecules of BCA form a complex with one $Cu^{1+}$ ion, which gives a purple color and has a strong absorbance at 562 nm. Bovine serum albumin (BSA) was used as standard.

Immunoprecipitation: Protein G Sepharose (Amersham) was used to immunoprecipitate GHR and phospho-STAT5b from the total nuclear extracts. Protein G is immobilized on sepharose beads and binds to the $F_c$ region of IgG, leaving the $F_{ab}$ region available for binding the antigen. For each sample, 60 μl protein G Sepharose slurry was used (approximately 30 μl clean sepharose). The sepharose was pooled in one 2 ml Eppendorf tube and washed in 3×1 ml of phosphate buffer saline (PBS) by centrifuging 3000 rpm for 2 minutes. Then the antibody was added, 5 μl/sample of either anti-GHR (MAb 263, AGEN) or anti phosphoSTAT5a/b, Y694/Y699 (Upstate Biotechnology). The sepharose with antibody was diluted with PBS and mixed end over end at room temperature for 2 hours. After that the sepharose slurry was divided in clean 2 ml Eppendorf tubes and washed in 1×1 ml PBS. Nuclear lysates were then thawed and added to the sepharose, 100-200 μl lysate from each sample. Dilution was made with 500 μl 2×lysis buffer with protease and phosphatase inhibitors as above, followed by mixing end over end at 4° C. over night. Next day each sample was washed two times with 1×lysis buffer and once with 1×lysis buffer and 125 mM Tris pH 6.8 in a mix 1:1. The proteins were then dissociated from the sepharose by adding 4×NuPAGE sample buffer (sodium dodecyl sulphate (SDS), bromphenol blue (BFB), glycerol) and 50 mM of the reducing agent dithiothreitol (DTT) (Sigma) to the samples and thereafter heating them at 70° C. for 10 minutes. The immunoprecipitated proteins in the supernatants could then be separated with gel electrophoresis.

Gel Electrophoresis: Extracted nuclear proteins were treated with 4×NuPAGE sample buffer and were then heated at 70° C. for 10 minutes. Samples analyzed in reduced form were also treated with 50 mM DTT in order to reduce disulfide bonds and break protein-protein interactions. Proteins were then separated on NuPAGE 4-12% Bis-Tris gel (Invitrogen). The gels were run at 200V and room temperature for 1 hour, running buffer Mops (50 mM MOPS, 50 mM Tris, 3.5 mM SDS, 1 mM EDTA). As a molecular weight marker SeeBlue Standard (Invitrogen) was used.

Western blot: Proteins were transferred to Hybond ECL nitrocellulose membranes (Amersham) at 4° C. and 100V for 1 hour with 1×NuPAGE transfer buffer (25 mM Bis-Tris, 25 mM Bicine, 1 mM EDTA, 10% EtOH). Membranes were then blocked with blocking buffer consisting of 1% milk in Tris Buffered Saline-Tween (TBST) (130 mM NaCl, 10 mM Tris-HCl pH 7.5, 0.05% Tween 20 (Amersham)) over night at 4° C. to prevent unspecific binding of antibodies to the membrane. Membranes were washed in TBST 2×5 minutes and then incubated with primary antibody for 1 hour at room temperature. After that, membranes were washed again in TBST 3×10 minutes, incubated with secondary antibody for 1 hour at room temperature and washed in TBST 4×10 minutes. The Horse Radish Peroxidase (HRP) coupled secondary antibodies were detected with ECL+ Plus and exposed on ECL Hyperfilm, both from Amersham.

Stripping and re-blotting: Membranes were stripped from antibodies by incubation in stripping buffer (62.5 mM Tris pH 6.5, 2% SDS, 100 mM β-Mercaptoethanol) at 50° C. for 30 minutes. They were washed for 2×10 minutes in large volumes of TBST and then blocked in blocking buffer (1% milk in TBST) at 4° C. over night. Re-blotting could then be performed with another antibody as described above. Primary antibodies used: Mouse monoclonal anti-GHR MAb 263 #174A-021 1:1000 (AGEN), rabbit polyclonal antisera anti-GHR directed to the intracellular part of GHR 1:5000 (Zhang et al., 2001), rabbit polyclonal antisera anti-GHR directed to the extracellular part of GHR (Biovitrum), rabbit polyclonal IgG anti-STAT5b (C-17) Lot #252 1:1000 (Santa Cruz Biotechnology), rabbit polyclonal IgG anti-phosphoSTAT5a/b (Y694/Y699) 1:1000 (Upstate Biotechnology). Secondary antibodies used: Goat anti-mouse IgG-HRP 1:2000 (Dako A/S), Sheep anti-mouse Ig-HRP 1:2000 (Amersham), Swine anti-rabbit IgG-HRP 1:3000 (Dako A/S).

Electrophoretic Mobility Shift Assay: Electrophoretic Mobility Shift Assay (EMSA) is a method used to investigate protein-DNA interactions. A DNA probe with a known sequence is end-labeled with $^{33}$P-ATP and then incubated with nuclear extracts. Proteins that bind specifically to the DNA-probe will reduce the mobility of the complex when separated on a non-denaturing poly acryl-amid gel and a shifted band can be seen. To identify proteins bound to the DNA-probe, an antibody can be added to the nuclear extract before incubation with the DNA-probe. If the antibody recognizes a protein that binds to the DNA, the mobility of the complex will be reduced even further and cause a supershift.

Labeling of oligonucleotides with $^{33}$P: Oligonucleotides were end-labeled with [γ-$^{33}$P] ATP (2500 Ci/mmol, Amersham or 3000 Ci/mmol, Perkin Elmer) by mixing 2 μl consensus oligonucleotide (1.75 pmol/μl, Promega or SGS DNA), 1 μl T4 Polynucleotide Kinase 10×Buffer (Promega), 1 μl T4 Polynucleotide Kinase (Promega), 1 μl [γ-$^{33}$P] ATP (Amersham or Perkin Elmer) and 5 μl nuclease free water (DEPC medium). The mixture was incubated at 37° C. for 10 minutes and the reaction was stopped by adding 1 μl 0.5 M EDTA. The volume was adjusted to 100 μl by adding 89 μl 0.05 M EDTA. To remove unincorporated [γ-$^{33}$P] ATP, the 100 μl aliquot was loaded on a NICK™ Column (Amersham Pharmacia Biotech AB) and labeled DNA was eluted with 2×400 μl 0.05 M EDTA. Specific activity was measured by mixing 2 μl $^{33}$P-labeled sample with 200 μl scintillation fluid and counting was performed in a Beta counter (Trilux1450).

Oligonucleotide sequences
GHRE:

```
5'-TAC GCT TCT ACT AAT CCA     (SEQ ID NO: 1)
TGT TCT GAG AAA TCA T-3'

3'-ATG CGA AGA TGA TTA GGT     (SEQ ID NO: 2)
ACA AGA CTC TTT AGT A-5'
```

OCT1:

```
5'-TGT CGA ATG CAA ATC ACT AGA A-3'   (SEQ ID NO: 3)

3'-ACA GCT TAC GTT TAG TGA TCT T-5'   (SEQ ID NO: 4)
```

AP2:

```
5'-GAT CGA ACT GAC CGC CCG CGG CCC    (SEQ ID NO: 5)
GT-3'

3'-CTA GCT TGA CTG GCG GGC GCC GGG    (SEQ ID NO: 6)
CA-5'
```

AP1:

```
5'-CGC TTG ATG AGT CAG CCG GAA-3'     (SEQ ID NO: 7)

3'-GCG AAC TAC TCA GTC GGC CTT-5'     (SEQ ID NO: 8)
```

Sequences of oligonucleotides that were annealed and used in EMSA or cloned to reporter vectors Pr2F linker with BglII/HindIII overhangs, used in EMSA:

```
                                          (SEQ ID NO: 9)
5'-GATCTAGATGCTTTCACAAACCCCACCCACAAA-3'

(SEQ ID NO: 10)
5'-AGCTTTTGTGGGTGGGGTTTGTGAAAGCATCTA-3'
```

Linker containing two potential AP2 sites, with KpnI/XhoI overhangs for cloning to Luc- and SEAP-reporter vectors:

```
5'-CTAGATGCTTTCACAAACCCCACCCACAAAATAGATGCTTTCACAA    (SEQ ID NO: 11)

ACCCCACCCACAAAAC-3'

5'-TCGAGTTTTGTGGGTGGGGTTTGTGAAAGCATCTATTTTGTGGGTGG   (SEQ ID NO: 12)

GGTTTGTGAAAGCATCTAGGTAC-3'
```

Linker containing two "Promega" AP2 sites, with KpnI/XhoI overhangs for cloning to Luc- and SEAP-reporter vectors.

5'-CGATCGAACTGACCGCCCGCGGCCCGTGATCGAACTGACCGCCCGC (SEQ ID NO: 13)
GGCCCGTC-3'

5'-TCGAGACGGGCCGCGGGCGGTCAGTTCGATCACGGGCCGCGGGCG (SEQ ID NO: 14)
GTCAGTTCGATCGGTAC-3'

Preparation of DNA binding reactions: For each reaction, 3-6 µg of nuclear protein extracted in EMSA buffer was mixed with 2 µl Gel Shift 5×Binding Buffer (Promega) and nuclease free water (DEPC medium) to 9 µl and then incubated for 10 minutes at room temperature. For super-shift analysis, nuclear extracts were pre-incubated with 1 µl of anti-GHR antibody or antisera for 1 hour at room temperature. To control the specificity of the protein-DNA binding, 400× excess of specific or unspecific un-labeled oligonucleotide was added to control reactions. The reactions were then incubated with 1 µl of $^{33}$P-end labeled GHRE (SGS DNA), AP1, AP2 or OCT1 consensus oligonucleotides (Promega) for 20 minutes at room temperature.

Gel electrophoresis of protein-DNA complexes: 2 µl of 6×loading buffer (3×TBE buffer, 32% glycerol, 0.06% BFB) was added to each sample, and the samples were then analyzed on a Novex 6% DNA retardation gel (Invitrogen). As running buffer 0.5×TBE (50 mM Tris pH 8.4, 45 mM Boric Acid, 0.5 mM EDTA (GIBCO)) was used and gels were run at 250 volt and room temperature for 19 minutes. Gels were fixed in a fix solution (30% ethanol, 10% acetic acid) and dried in a gel dryer. They were then analyzed with phosphor imager instrumentation (STORM 860 (Molecular Dynamics) and Image Quant 5.0).

EMSA—Western Blot: EMSA was performed as described above, but instead of drying the gel and expose it to a phosphor imager screen, the proteins in the gel were transferred to a nitrocellulose membrane and blotted with an anti-GHR antibody as in a regular Western Blot, as described. To confirm that the proteins were transferred to the membrane, the membrane was immersed in Ponceau S Solution (Sigma), which stains all proteins red.

Example 1

GHR and STAT5 are Present in Nuclear Extracts

Figure 3A:
FIG. 3A depicts a Western blot of nuclear extracts from GHR-transfected WRL-68 cells, using a rabbit anti-GHR antibody as a primary antibody, visualized by a pig anti-rabbit secondary antibody coupled to HRP.
Figure 3B:
FIG. 3B depicts a control Western blot of nuclear extracts from GHR-transfected WRL-68 cells, using the pig anti-rabbit secondary antibody alone.
Figure 3C:
FIG. 3C depicts a Western blot of nuclear extracts from WRL-68 cells, using a rabbit anti-GHR antibody as a primary antibody, visualized by a pig anti-rabbit secondary antibody coupled to HRP. Although GHR is present in nuclear extracts from both transfected and untransfected cells, regardless of treatment, the amount of the receptor is higher in transfected cells.
Figure 3D:
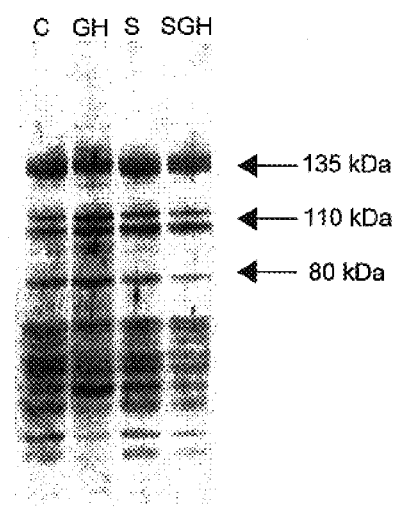
FIG. 3D depicts a Western blot of nuclear extracts from HX rat liver cells, using a rabbit anti-GHR antibody as a primary antibody, visualized by a pig anti-rabbit secondary antibody coupled to HRP. The amount of GHR in HX rat liver cells is as high as in transfected WRL-68 cells.

Cultured cell lines usually exhibit low amounts of endogenously produced GHR (FIG. 3C), whereas liver tissue contains high amounts of receptors (FIG. 3D). To detect the GHR in the nucleus, nuclear proteins were separated with gel electrophoresis and visualized in Western Blot. When blotted with a polyclonal antibody against the intracellular part of the receptor, the GHR could be detected as three distinct bands in all fractions of the examined cell types (WRL-68, GHR-transfected WRL-68 and HX rat livers. None of the bands appeared as a result of unspecific binding of the secondary antibody (pig anti-rabbit, FIG. 3B).

The Western Blot membrane with non-transfected WRL-68 total nuclear extracts was re-blotted with a polyclonal antibody against STAT5, and two bands of 60 and 100 kDa, respectively, could be seen. The 100-kDa band probably represented intact STAT5 monomers, while the 60-kDa band could be a cleaved form of STAT5 (Data not shown).

Example 2

Transfection of WRL-68 Cells with Full-length GH-receptor Increase Protein Interactions with GHRE, AP2, OCT1 and Pr2F DNA Probes GH-receptor transfected and non-transfected WRL-68 nuclear extracts were incubated with anti-GHR antibody and $^{33}$P-GHRE (SEQ ID NOS: 1 and 2), $^{33}$P-AP2 (SEQ ID NOS: 5 and 6) or $^{33}$P-OCT1 (SEQ ID NOS: 3 and 4) or $^{33}$P-Pr2F (SEQ ID NOS: 9 and 10) consensus oligo-nucleotides and analyzed in EMSA to elucidate any possible interactions of the GHR with proteins binding to these DNA probes. For control, nuclear extracts not incubated with anti-GHR were also analyzed EMSA with the GHRE probe showed several shifted bands in both GHR-transfected and non-transfected cells. The specificity of the bands was shown by incubating with 400 times excess of unlabelled specific or unspecific probe (see FIG. 1 and FIG. 2). No effect of hGH stimulation could be identified. Interestingly, transfection with full-length GHR seemed to increase the intensity of the top shifted band. The protein-DNA interaction in this band was disrupted by BVTA (N-[5-(aminosulfonyl)-2-methylphenyl]-5-bromo-2-furamide), since the intensity of the band was decreased in extracts from BVTA stimulated cells, and a lower band appeared representing a smaller complex with higher mobility. No difference in binding could be seen when incubating these extracts with anti-GHR antibody. In non-transfected cells, incubation of nuclear extracts with anti-GHR seemed to increase protein binding to the GHRE probe. The increased intensity of these bands could also be due to a supershift of the weak, lower bands. There was also a vague indication of a supershift of the GHRE top weak band in non-transfected cells, but in this case no effect from BVTA could be seen. Incubation with antibody only and labeled GHRE probe showed that the antibody did not interact with DNA itself.

Figure 1B:
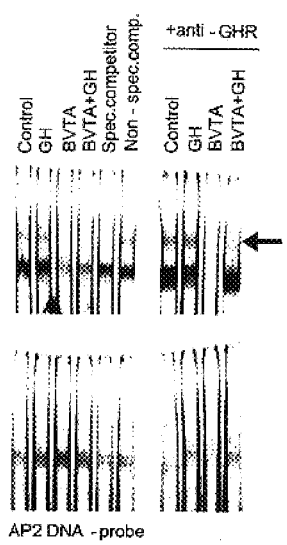
FIG. 1B depicts the results of EMSA in nuclear extracts from GHR transfected and non-transfected WRL-98 cells incubated with an anti-GHR antibody and AP2 DNA probes (SEQ ID NOS:5 and 6).
Figure 2A:
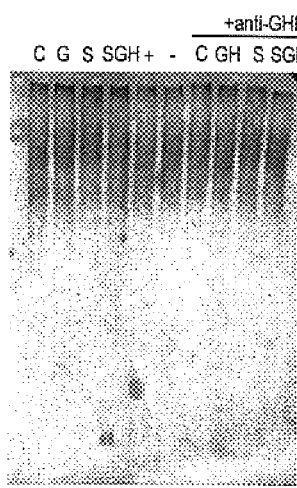
FIG. 2A depicts the total protein on filter as visualized by Ponceau staining.
Figure 2B:
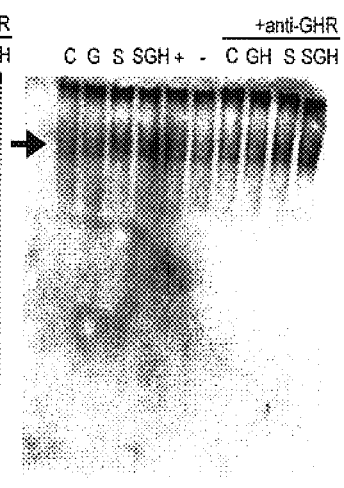
FIG. 2B depicts a Western blot with an anti-GHR antibody.
Figure 2C:
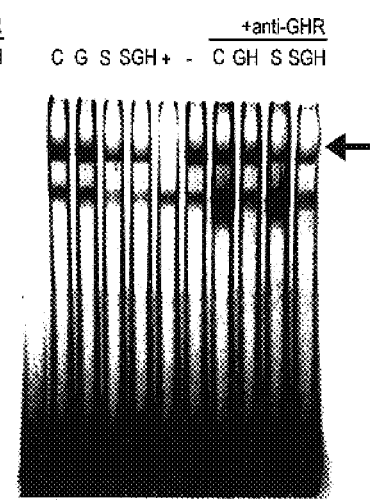
FIG. 2C depicts an EMSA gel, showing that the GHR is present in the shifted band.

EMSA with AP2 DNA probe and non-transfected WRL-68 cells showed one shifted band that could not be competed out (FIG. 1B). In EMSA with AP2 and GHR-transfected WRL-68, an additional band could be seen, which was specific since it was competed by 400× excess of unlabeled AP2 probe (FIG. 1B, arrow). When incubating these nuclear extracts with an anti-GHR antibody, this specific band increased in intensity, suggesting an enhanced interaction between the protein complex and the AP2 DNA probe. As with GHRE, BVTA broke the protein-DNA interaction represented by the top specific band, since this band disappeared in extracts from BVTA stimulated cells. As before, no effects could be seen from hGH stimulation compared to control extracts. The antibody itself showed no interaction with the DNA probe.

EMSA with OCT1 DNA probe and the two WRL-68 cell types showed two shifted bands (FIG. 1A). The top shifted band represented specific binding, since it was competed with 400 times excess of un-labeled OCT1 probe. As with GHRE and AP2, the intensity of the top band was increased in extracts from GHR-transfected WRL-68 cells (FIG. 1A, arrow), but in contrast to AP2, incubation of extracts with an anti-GHR antibody did not affect the binding of nuclear proteins to the OCT1 DNA probe. No effects could be seen in nuclear extracts from hGH stimulated cells compared to un-stimulated control cells. Also in this case BVTA broke some protein-DNA interactions; the intensity of the top specific band was decreased in extracts from BVTA treated cells. As with GHRE and AP2, the antibody itself showed no interaction with the DNA probe.

Non-transfected WRL-68 nuclear extracts were analyzed with AP1 DNA probe (SEQ ID NOS: 7 and 8) as a control since AP1 is activated via GH-activated MAP kinase. One shifted band could be seen in all fractions showing an activated AP1 transcription factor, and no effects could be seen from either hGH or BVTA. Incubation with a GHR-antibody resulted in somewhat fainter bands.

EMSA was performed with AP2 and OCT1 probes together with nuclear extract from GHR-transfected WRL-68 cells. The separated complexes were transferred to a nitrocellulose membrane. Blotting the membranes with an anti-GHR antibody indicated the presence of GHR in a blurred band that, when compared to the EMSA gels, seemed to correspond to the specific shifted bands of OCT1 and AP2 oligonucleotide. The correlation of the GHR bands and the OCT1- and AP2-shifted bands indicated that GHR is present in the OCT1 shifted complex, and possibly also in the AP2 shifted complex.

Example 3

Incubation of Rat Liver Nuclear Extracts with Anti-GHR Antibodies Enhances Protein Binding to an AP2 DNA Probe HX rat liver nuclear extracts were incubated with anti-GHR and $^{33}$P-GHRE, $^{33}$P-AP2 or $^{33}$P-OCT1 consensus oligonucleotides and analyzed in EMSA. For control, nuclear extracts not incubated with anti-GHR were also analyzed. Extracts from two control animals and two hGH stimulated animals were used in the assays.

Figure 1C:
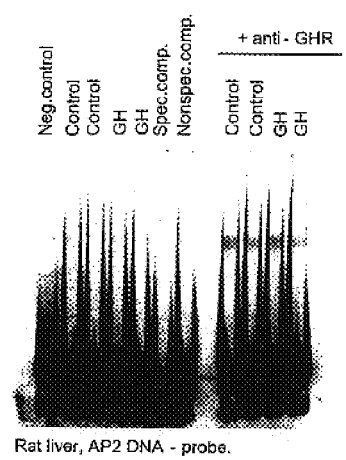
FIG. 1C depicts the results of EMSA in nuclear extracts from rat liver cells incubated with an anti-GHR antibody and AP2 DNA probes (SEQ ID NOS:5 and 6).
Figure 1D:
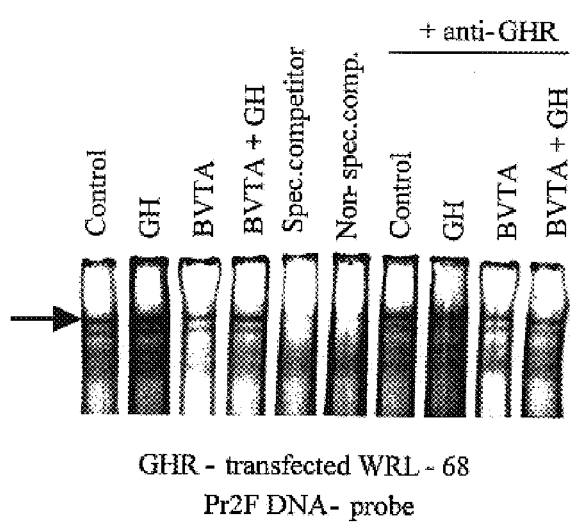
FIG. 1D depicts the results of EMSA in nuclear extracts from GHR transfected and non-transfected WRL-98 cells incubated with an anti-GHR antibody and Pr2F DNA probes (SEQ ID NOS:9 and 10).
Figure 1E:
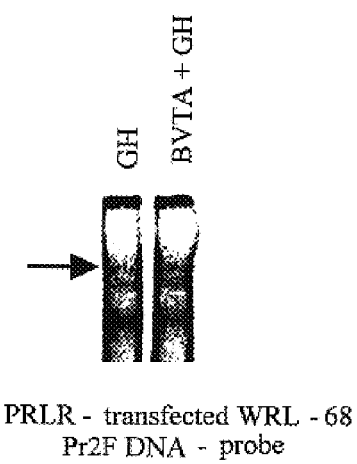
FIG. 1E depicts the results of EMSA in nuclear extracts from prolactin receptor transfected WRL-98 cells incubated with Pr2F DNA probes (SEQ ID NOS: 9 and 10).
Figures 1F, 1G, 1H:
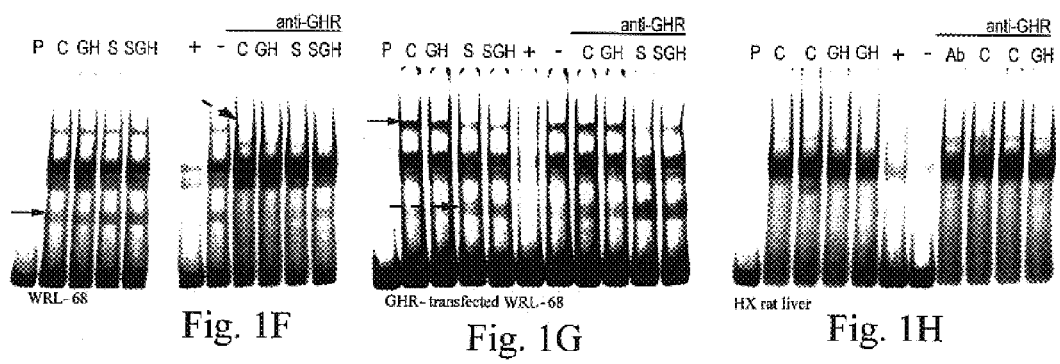
FIG. 1F depicts the results of EMSA in nuclear extracts from WRL-98 cells incubated with an anti-GHR antibody and growth hormone response element DNA probes (SEQ ID NOS: 1 and 2). Free probe (P) was used as a negative control. To confirm specific protein-DNA interaction, 400× excess of un-labeled specific (+) or non-specific (−) probe was added to the reaction. Investigation of possible supershifts was made by incubating the extracts with an anti-GHR antibody (MAb 263) prior to the addition of the labeled DNA-probe. Non-specific competition was not performed; instead antibody only was incubated with the DNA-probe (Ab). S=BVTA.
FIG. 1G depicts the results of EMSA in nuclear extracts from GHR transfected WRL-98 cells incubated with an anti-GHR antibody and growth hormone response element DNA probes (SEQ ID NOS: 1 and 2). Free probe (P) was used as a negative control. To confirm specific protein-DNA interaction, 400× excess of un-labeled specific (+) or non-specific (−) probe was added to the reaction. Investigation of possible supershifts was made by incubating the extracts with an anti-GHR antibody (MAb 263) prior to the addition of the labeled DNA-probe. Non-specific competition was not performed; instead antibody only was incubated with the DNA-probe (Ab). S=BVTA.
FIG. 1H depicts the results of EMSA in nuclear extracts from HX rat liver cells incubated with an anti-GHR antibody and growth hormone response element DNA probes (SEQ ID NOS: 1 and 2). Free probe (P) was used as a negative control. To confirm specific protein-DNA interaction, 400× excess of un-labeled specific (+) or non-specific (−) probe was added to the reaction. Investigation of possible super-shifts was made by incubating the extracts with an anti-GHR antibody (MAb 263) prior to the addition of the labeled DNA-probe. Non-specific competition was not performed; instead antibody only was incubated with the DNA-probe (Ab).

EMSA with GHRE and OCT1 DNA probes did not show any differences in protein-DNA binding either with hGH stimulation or with pre-incubation of nuclear extracts with an anti-GHR antibody. In contrast, EMSA with an AP2 DNA probe showed an enhanced protein-DNA interaction when nuclear extracts were incubated with an anti-GHR antibody (FIG. 1C). As mentioned above, this effect was also seen with GHR-transfected WRL-68 cells and AP2 probe (FIG. 1B). No difference in protein-DNA binding could be seen in extracts from hGH stimulated animals compared to control animals though. To confirm that the increased protein-DNA interactions seen in anti-GHR incubated HX rat liver nuclear extracts were specific for anti-GHR antibodies, other antibodies against the GHR were tested. The experiment was repeated with two different rabbit polyclonal antibodies, one directed against the extracellular part and one against the intracellular part of the GHR. Both of these antibodies showed the same enhancing effect of protein-DNA interaction as the first antibody used which was a mouse monoclonal antibody against the extracellular part of the GHR. None of the antibodies interacted with the DNA probe themselves. To confirm that the enhanced protein-DNA interaction seen was specific for anti-GHR antibodies and not caused by any antibody, the same experiment was performed with an anti-PKC antibody. Anti-PKC did not enhance the protein-DNA interaction.

References

Ausubel, F. M., et al. (1993). In: *Current Protocols in Molecular Biology*, Vol. 2, John Wiley and Sons, New York.

Bichell, D. P., Kikuchi, K., Rotwein, P. (1992). Growth Hormone Rapidly Activates Insulin-Like Growth Factor I Gene Transcription in *Vivo. Mol. Endocrin.* 6:1899-1908

Clevenger, C. V., Furth, P., Hankinson, S. E., Shuler, L. (2003). The role of prolactin in mammary carcinoma. *Endocrine Rev.* 24:1-27

Dignam, J. D., Lebowitz, R. M., Roeder, R. (1983). Accurate transcription initiation by RNA polymerase II in a soluble extract from isolated mammalian nuclei. *Nucl. Acids Res.* 11:1475-1489.

Graichen, R., Sandstedt, J., Goh, E. L. K., Isaksson, O. G. P., Törnell, J., Lobie, P. E. (2003). the Growth Hormone-binding Protein Is a Location-dependent Cytokine Receptor Transcriptional Enhancer. *J. Biol. Chem.* 278:6346-6354

Helander, H., Gustafsson, J-Å., Mode, A. (2002). Possible involvement of truncated signal transducer and activator of transcription-5 in the GH pattern-dependent regulation of CYP2C12 gene expression in rat liver. *Mol. Endocrinology* 16:1598-1611

Jiang, L.-W., Schindler, M. (1990). Nucloecytoplasmic transport is enhanced concomitant with nuclear accumulation of epidermal growth factor (EGF) binding activity in both 3T3-1 and EGF receptor reconstituted NR-6 fibroblasts. *J. Cell Biol.* 110:559-568

Le Stunff, C., Thomas, M. J., Rotwein, P. (1995). Rapid Activation of Rat Insulin-Like Growth Factor-I Gene Transcription by Growth Hormone Reveals No Changes in Deoxyribonucleic Acid-Protein Interactions within the Second Promoter. *Endocrinology* 136:2230-2237

Lobie, P. E., Wood, T. J. J., Chen, C. M., Waters, M. J., Norstedt, G. (1994). Nuclear Translocation and Anchorage of the Growth Hormone Receptor. *J. Biol. Chem.* 269:31735-31746

Nolten, L. A., Steenbergh, P. H., Sussenbach, J. S. (1995). Hepatocyte nuclear factor 1α activates promoter 1 of the human insulin-like growth factor 1 gene via two distinct binding sites. *Mol. Endocrinology* 9: 1488-1499

Pfisterer, P., Ehlermann, J., Hegen, M., Schorle, H. (2002). A Subtractive Gene Expression Screen Suggests a Role of Transcription Factor AP-2α in Control of Proliferation and Differentiation. *J. Biol. Chem.* 277:6637-6644

Podlecki, D. A, Smith, R. M., Kao, M., Tsa, M., Huecksteadt, T., Brandenburg, D., Lasher, R. S., Jarret, L., Olefsky, J. M. (1987). Nuclear translocation of the insulin receptor. *J. Biol. Chem.* 262:3362-3368

Thomas, M. J., Kikuchi, K., Bichell, D. P., Rotwein, P. (1994) Rapid activation of rat insulin-like growth factor-1 gene transcription by growth hormone reveals no alterations in deoxyribonucleic acid-protein interactions within the major promoter. *Endocrinology* 135:1584-1592

Werling, U., Schorle, H. (2002). Transcription Factor gene AP-2γ Essential for Early Murine Development. *Mol. Cell. Biol.* 22:3149-3156

Wood, T. (1996). Growth hormone, JAKs and STATs: a model cytokine signal transduction system. Thesis.

Zhang, Y., Guan, R., Jiang, J., Kopchick, J. J., Black, R. A., Baumann, G., Frank, S. (2001). Growth hormone (GH)-induced dimerization inhibits phorbol ester-stimulated GH receptor proteolysis. *J. Biol. Chem.* 276: 24565-24573

OTHER EMBODIMENTS

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. A method for identifying an agent that modulates a nuclear interaction between growth hormone receptor and a nuclear factor, the method comprising:
    contacting a cell with a candidate agent;
    preparing a nuclear extract of the cell; and
    analyzing the nuclear extract to determine whether the candidate agent modulates a nuclear interaction between growth hormone receptor and a nuclear factor that interacts with growth hormone receptor, with the proviso that the nuclear factor is other than STAT5.

2. The method of claim 1, comprising:
    contacting the cell with the candidate agent, wherein the candidate agent modulates the interaction between growth hormone receptor and the nuclear factor;
    measuring, in the presence of the candidate agent, a biological effect of a growth hormone receptor binding compound in the cell; and
    determining whether the candidate agent modulates the biological effect of the growth hormone receptor binding compound in the cell.

3. The method of claim 1, wherein the candidate agent inhibits the interaction between growth hormone receptor and the nuclear factor.

4. The method of claim 1, wherein the candidate agent stimulates the interaction between growth hormone receptor and the nuclear factor.

5. The method of claim 2, wherein the growth hormone receptor binding compound is growth hormone.

6. The method of claim 1, wherein the nuclear factor is AP2, OCT1, or Pr2F.

7. The method of claim 2, comprising determining the expression of a reporter gene coupled to a promoter comprising a response element for a nuclear factor selected from the group consisting of AP2, OCT1, and Pr2F.

* * * * *